United States Patent [19]

Uhlen et al.

[11] Patent Number: 5,330,914
[45] Date of Patent: Jul. 19, 1994

[54] APPARATUS AND METHOD FOR AUTOMATED PURIFICATION OF EXTRA-CHROMO-SOMAL DNA FROM A CELL SUSPENSION IN A CONTAINER

[75] Inventors: Mathias Uhlen, Upsala; Tomas Moks, Täby, both of Sweden

[73] Assignee: CEMU Bioteknik AB, Upsala, Sweden

[21] Appl. No.: 603,717

[22] PCT Filed: Mar. 17, 1989

[86] PCT No.: PCT/SE89/00144

§ 371 Date: Nov. 26, 1990

§ 102(e) Date: Nov. 26, 1990

[87] PCT Pub. No.: WO89/09265

PCT Pub. Date: Oct. 5, 1989

[30] Foreign Application Priority Data

Mar. 24, 1988 [SE] Sweden .................................. 8801098

[51] Int. Cl.⁵ .......................... E12N 1/08; C12M 1/36; C07H 15/12
[52] U.S. Cl. ........................ 435/270; 435/289; 536/25.4; 935/19
[58] Field of Search ....................... 435/270, 289, 290; 935/19; 536/27, 25.4

[56] References Cited

U.S. PATENT DOCUMENTS 5,057,426 10/1991 Henco et al. ...................... 435/270

FOREIGN PATENT DOCUMENTS 2215533 3/1987 European Pat. Off. .
2245945 11/1987 European Pat. Off. .

OTHER PUBLICATIONS

Just et al. "Rapid High-Yield Purification of Plasmids by Alkaline Extraction ... " BioTechniques vol. 1 No. 3 (1983) pp. 136–140.
Micard et al "Purification of RNA-Free Plasmid DNA ... " Analytical Biochemistry vol. 148 (1985) pp. 121–126.
Chemical Abstracts, 103, 1985, 67838t (Micard et al.).
Chemical Abstracts, 103, 1985, 192722b (Ranhand et al.).
Chemical Abstracts, 100, 1984, 31842P (Just et al.).

Primary Examiner—Michael G. Wityshyn
Assistant Examiner—Timothy J. Reardon
Attorney, Agent, or Firm—Bacon & Thomas

[57] ABSTRACT

This invention relates to an apparatus for automatic purification of extra-chromosomal DNA from a cell suspension in a container. The apparatus comprises a device for introducing the cell suspension from a container into a chamber; a device for agitating the contents of the chamber; a device for introducing a lysing solution to the chamber to lyse the cells therein; a device for introducing a precipitating solution into the chamber to precipitate chromosomal DNA and, optionally, proteins and cellular debris therein; a device for feeding the liquid contents of the chamber through a filter to a collecting system; a device for purifying extra-chromosomal DNA from the contents of the collecting device; a device for introducing a dissolving solution into the chamber to dissolve the precipitate remaining therein, and a device for feeding the dissolved precipitate to waste.

10 Claims, 1 Drawing Sheet

APPARATUS AND METHOD FOR AUTOMATED PURIFICATION OF EXTRA-CHROMO-SOMAL DNA FROM A CELL SUSPENSION IN A CONTAINER

The invention relates to an apparatus and a method for automatic purification of extra-chromosomal DNA from a cell suspension in a container.

It is known from Birnboim and Doly (Nucl Acids Res 7, 1513-1523, 1979) that plasmid DNA can be purified from Escherichi coli. The bacterial cells are first lysed in an alkaline medium containing a detergent. This is followed by a neutralizing step which yields the plasmid DNA in soluble form while most proteins, cell debris and chromosomal DNA precipitate. Plasmid DNA is then recovered from the mixture by centrifugation and a pure plasmid fraction is obtained by subsequent purification. Kieser (Plasmid 12, 19-36, 1984) has described a similar method, involving a combination of heat treatment and alkali treatment, which gave improved purification of plasmid DNA and less contaminating RNA. In these known methods, the purification involves several separate steps, such as for instance extractions and centrifugations, thus requiring considerable investments in equipment and operator time.

An automated plasmid purification work station based on a laboratory robot has been described by de Bonville and Riedel (Advances in Laboratory Automation Robotics, 1986, ed. Strimatis and Hawk, Zymark Corp., Hopkinton, Ma., pp353-360). That system is based on a number of laboratory unit operations and the robot uses several hardware stations, including a centrifuge, pipettes, capping devices, sample tubes, tip racks, microtiterplate etc.

Although this workstation is automated the system has several disadvantages. Firstly the system has to be set up with tip racks, sample tubes, supernatant tubes etc., which is labour intensive. Secondly, a considerable amount of disposable material is used which increases the expenses for each plasmid purified by the system. Thirdly, several mechanical operations are involved and this might cause technical problems in routine use.

An automated nucleic acid extractor has been described (EP-O 245 945) for extracting and purifying nucleic acids from cells without the use of centrifugation. In the method (described in EP-O 215 533) a lysate is created and mixed with a phenol-based solvent system and then heated to promote phase separation. The lower organic phase is removed and the upper aqueous phase is repeatedly extracted. The aqueous phase is finally dialyzed to further purify the nucleic acid solution. The method is used for extraction of high molecular weight DNA (about $10^8$ daltons) from eukaryotic cells such as peripheral blood lymphocytes and liver cells. Thus, the method is well suited for extraction of chromosomal DNA from cells, but is not adapted for purification of extrachromosomal DNA from bacteria, such as plasmid DNA, as the unit operations used in the method can not efficiently separate chromosomal from extra-chromosomal DNA.

The object of the invention is to bring about an apparatus and a method for purification of extrachromosomal DNA from bacteria that do not have these disadvantages.

This is attained in that the apparatus according to the invention for automatic purification of extra-chromosomal DNA from a cell suspension in a container, comprises
- means for introducing the cell suspension from the container into a chamber,
- means for agitating the contents of the chamber,
- means for introducing a lysing solution into the chamber to lyse the cells therein,
- means for introducing a precipitating solution into the chamber to precipitate chromosomal DNA and, optionally, proteins and cell debris therein,
- means for feeding the liquid contents of the chamber through a filter to a collecting device,
- means for purifying extra-chromosomal DNA from the contents of the collecting device,
- means for introducing a dissolving solution into the chamber to dissolve the precipitate remaining therein, and
- means for feeding the dissolved precipitate to waste.

The method according to the invention for automatic purification of extra-chromosomal DNA from a cell suspension, comprises
- introducing the cell suspension into a chamber,
- introducing a lysing solution into the chamber and mixing it with the contents thereof to lyse the cells therein,
- introducing a precipitating solution into the chamber and mixing it with the contents thereof to precipitate chromosomal DNA and, optionally, proteins and cell debris therein,
- filtering the contents of the chamber through a filter and feeding the liquid contents to a collecting device,
- purifying extra-chromosomal DNA from the contents of the collecting device,
- introducing a dissolving solution into the chamber and mixing it with the contents thereof to dissolve the precipitate remaining therein, and
- feeding the dissolved precipitate from the chamber to waste.

BRIEF DESCRIPTION OF THE DRAWINGS

The apparatus and method according to the invention will be described more in detail below with reference to the accompanying drawings on which

Figure 1:
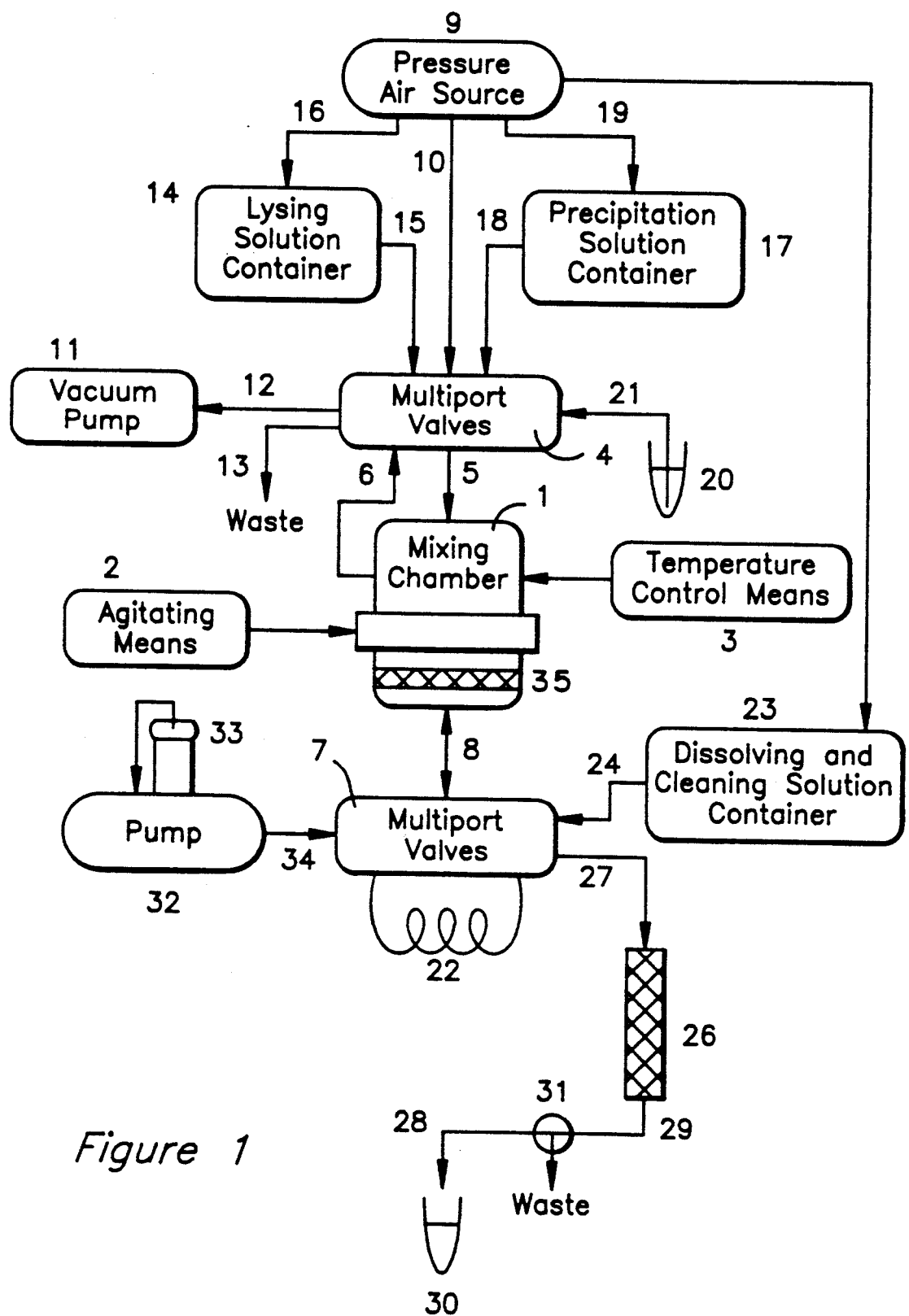
FIG. 1 shows a schematic block diagram of an embodiment of an apparatus according to the invention In the block diagram (FIG. 1), 1 denotes a mixing chamber around which the apparatus according to the invention, is built up. The mixing chamber 1 is provided with agitating means 2, e.g. vibrating or rotating means, to facilitate mixing of the contents of the chamber 1. Moreover, the chamber 1 is provided with means 3 to control the temperature of the chamber 1. The temperature control means 3 can comprise an electric temperature control device or means for supplying heating-/cooling liquids to a space between the chamber 1 and a jacket (not shown) surrounding the chamber 1.

An inlet port at the top of the chamber 1 is connected to an outlet port of multiport valves 4 via a tubing 5, while an outlet port in the upper part of the chamber 1 is connected to an inlet port of the multiport valves 4 via a tubing 6.

An outlet/inlet port at the bottom of the chamber 1 is connected to an inlet/outlet port of mult-port valves 7 via a tubing 8.

The chamber 1 may be provided with level sensor means (not shown) to sense the liquid level in the chamber 1.

At the bottom of the chamber 1, a filter 35 is provided in the embodiment shown. This filter 35 must not necessarily be located within the chamber 1, but can instead be located in the tubing 8.

The multiport valves 4 also exhibit an inlet port connected to a source 9 of pressure air via a tubing 10, and an outlet port connected to a vacuum pump 11 via a tubing 12. Another outlet port of the multiport valves 4 is connected to waste via a tubing 13.

Moreover, the multiport valves 4 are connected with one of its inlet ports to a lysing solution container 14 via a tubing 15. The container 14 is pressurized in that it is connected to the pressure air source 9 via a tubing 16.

Another inlet port of the multiport valves 4 is connected to a precipitating solution container 17 via a tubing 18. The container 17 is also pressurized in that it is connected to the pressure air source 9 via a tubing 19.

Instead of pressurizing the containers 14 and 17, a pump (not shown) may be used to move the respective solutions.

A tube or vial 20 containing a cell suspension from which extra-chromosomal DNA is to be purified may be automatically connected to an inlet port of the multiport valves 4 via an automatic injector or sampler 21 which is just schematically indicated. It is to be understood that there can be a number of vials 20 from which extra-chromosomal DNA is to be purified in sequential order.

The multiport valves 7 exhibit an inlet port and an outlet port between which a sample loop 22 of predetermined volume is connected in the embodiment shown.

A container 23 containing a dissolving and cleaning solution is connected to an inlet port of the multiport valves via a tubing 24. The container 23 is also pressurized in that it is connected to the pressure air source 9 via a tubing 25.

The inlet end of a chromatographic gel filtration column 26 is connected to an outlet port of the multiport valves 7 via a tubing 27, while the outlet end of the column 26 is connected to a drip nozzle 28 of a fraction collector (not shown) via a tubing 29. Drops of purified extra-chromosomal DNA from the drip nozzle 28 are collected in a vial 30 of the fraction collector. It is to be understood that there can be a number of vials 30 to collect extra-chromosomal DNA extracted in sequence from the cell suspension vials 20.

In the tubing between the outlet end of the column 26 and the drip nozzle 28 of the fraction collector (not shown), a two-way valve 31 is inserted to connect the outlet end of the column 26 to either the drip nozzle 28 or waste.

An eluant for the chromatographic column 26 is supplied by a pump 32 from an eluant container 33 via a tubing 34 to an inlet port of the multiport valves 7.

The multiport valves 4 and 7 as well as the agitating means 2, the temperature control means 3, the sampler 21, the pump 32, and the fraction collector (symbolized by 28 and 30) are all controlled by a control unit (not shown) in a manner known per se.

The apparatus shown on the drawing, operates as follows to automatically purify extra-chromosomal DNA from a cell suspension in the vial 20:

The cell suspension is sucked from the vial 20 into the mixing chamber 1 in that the mixing chamber 1 has been evacuated by the vacuum pump 11 via the tubings 12 and 6 through the multiport valves 4. Thus, the cell suspension is sucked up by the sampler 21 and enters the mixing chamber 1 through the tubing 5 via the multiport valves 4.

If desired, the cell suspension may, optionally, be concentrated by filtering the suspension through the filter 35 in the mixing chamber 1.

The cells in the cell suspension are, then, lysed in that a predetermined amount of the lysing solution from the lysing solution container 14, is introduced by pressure air from the pressure air source 9 into the mixing chamber 1 via the tubing 15, the multi-port valves 4 and the tubing 5.

Then, the mixing chamber 1 is agitated by means of the agitating means 2 to mix the cell suspension and the lysing solution within the mixing chamber 1.

Optionally, the mixing chamber 1 is heated by means of the temperature control means 3 during the lysing of the cells. To precipitate chromosomal DNA, proteins and cell debris from the contents of the mixing chamber 1, a predetermined amount of the precipitating solution from the precipitating solution container 17 is, then, introduced into the mixing chamber 1 by pressure air from the pressure air source 9 via the tubing 18, the multiport valves 4 and the tubing 5.

After agitating the mixing chamber 1 by means of the agitating means 2, and, optionally, cooling the mixing chamber 1 by means of the temperature control means 3, the contents of the mixing chamber 1 is filtered through the filter 35 by means of pressure air from the pressure air source 9 via the tubing 10, the multi-port valves 4 and the tubing 5. The liquid contents of the mixing chamber 1 is collected by the loop 22 via the tubing 8 and the multiport valves 7, while precipitated chromosomal DNA, proteins and cell debris will remain on the filter 35.

To purify extra-chromosomal DNA, the contents of the loop 22 is applied to the chromatographic column 26 by means of the pump 32.

Impure fractions are supplied to waste by the valve 31, while pure extra-chromosomal DNA is collected in the vial 30 from the drip nozzle 28.

At the same time as the chromatographic purification takes place, the precipitate remaining on the filter 35 and within the mixing chamber 1, is dissolved in that a predetermined amount of the dissolving and cleaning solution from the container 23 is introduced by pressure air from the pressure air source 9 into the mixing chamber 1 through the tubing 24, the multiport valves 7 and the tubing 8.

After agitating the mixing chamber 1 by means of the agitating means 2 to dissolve and loosen all the precipitate, the dissolved precipitate is supplied to waste by means of pressure air from the pressure air source 9 via the tubing 10, the multiport valves 4, and the tubings 5, 6 and 13.

The mixing chamber 1 is, then ready to receive another cell suspension from the sampler 21 to start a new extraction cycle.

Also, the column 26 is regenerated in that the dissolving and cleaning solution from the container 23 is pumped to waste through the column 26 by means of the pump 32.

After that, the column 25 is also ready for a new purification cycle.

Instead of the column 26, means can be provided to add a DNA precipitating agent to the contents of the loop 22 to purify extra-chromosomal DNA by precipitation in a manner known per se.

The means for purifying extra-chromosomal DNA may also comprise adsorbing means, e.g. a solid adsorption matrix, for adsorbing purified extra-chromosomal DNA from the contents of the loop 22.

The purification mentioned in the above two paragraphs is suitably carried out in a separate chamber or container (not shown).

EXAMPLE

Reagent solutions
R1: 4% SDS, 50 mM EDTA
R2: 0.7 M NaOH
R3: 4.5 M NaAc, 3 M HAC
R4: 0.025 M Tris (pH 8.0), 0.01 M EDTA
R5: 0.2 M NaOH
ES: 0.1 M NaCl, 0.001 M EDTA, 0.01 M Tris (pH 8.0)
Column packing: Sephacryl S-500 HR (Pharmacia AB)
Processor: LCC-500 (Pharmacia AB)
Fraction Collector: FRAC 100 (Pharmacia AB)
Automatic Injector: ACT 100 (Pharmacia AB)
Multiport Valves: MW7 and MW8 (Pharmacia AB)
Agitation unit: Vortex Genie 2 (Scientific Industries)
Pump: P-500 (Pharmacia AB)
Two-way valves: PSV-100 (Pharmacia AB)
Filter chamber: containing 0.45 μgm HVLP Millipore
Water bath: 2019 Multiheat (LKB)
Valves for heating water: LAPS ¼", LTPE ¼" (Burkert)

The "SEPHACRYL S-500 HR" used for the column packing is a well-known polyacrylamide gel which is a copolymer of allyl dextran and N, N' methylene bisacrylamide.

10 overnight cultures of E.coli. HB101 (Maniatis et al., Molecular cloning, Cold Spring Harbor, N.Y.) containing plasmid pUC 8 (Viera and Messig, Gene 19, 259-268, 1982) with different inserts (grown at 37° C. in 5 ml of Tryptic Soy Broth (30 g/l Difco)) were transferred to the autoinjector unit. The cell suspension from the first tube was introduced into the chamber by vacuum. By applying air pressure the cell suspension was concentrated using the filter which retained the cells while the culture medium was discharged. A sensor was used to detect when approximately 1.5 ml of liquid was left in the chamber. The cells in the chamber were resuspended by repeated on/off vortex sequences. A 0.6 ml reagent loop was loaded with reagent solution R1, which was then transferred to the chamber. Reagent solution R2, was introduced in the same way and the cells were then subjected to lysis for about 3 minutes at a temperature of about 50° C. with repeated on/off mixing. During the lysis chromosomal DNA is denatured and large RNAs and proteins are degraded. The sample loop was then washed with reagent solution R4 before it was filled with R3 which was transferred to the chamber as described above. In this way, proteins and chromosomal DNA was precipitated with repeated on/off mixing. The lysate were filtered to the 2 ml sample loop by applying air pressure. The 2 ml DNA sample was then injected into the eluent flow from the pump to the column containing Sephacryl S-500.

The plasmid DNA elutes in the void volume and was collected for further analysis or preparative work, while the degraded RNA and proteins are retained and washed to waste. In parallel with the chromatographic separation step, the chamber was regenerated by solution R5 which was introduced into the chamber from below. When the separation step was finished the column was regenerated by solution R5. The complete cycle was then repeated with the remaining nine samples.

A complete cycle for introducing the cell suspension into the chamber to complete regeneration of the chamber and the column took less than ten minutes. The complete purification involving ten samples therefore took approximately ninety minutes under which no supervision or manual labor was needed. The ten purified plasmids were analysed by 1% agarose gel electrophoresis (Maniatis et al., see above) 500 ng of standard lambda HindIII DNA (Pharmacia AB) was used as a marker. 15 μl of total 1.5 ml of purified sample was applied to the gel. The results showed that the yields are approximately the same in the ten samples (more than 20 μg of plasmid DNA for each sample).

The collected plasmid DNA fractions were further analyzed by dividing approximately 500 ng of each sample into two tubes and restricting one of the duplicates containing 250 ng with 2 units of restriction enzyme EcoRI (Pharmacia, Uppsala, Sweden) and incubating for 60 minutes at 37° C. (total volume 0.04 ml). The material, before and after cleavage was used to transform competent E.coli HB101 for ampicillin (70 mg/l) resistance. This experiment demonstrates that cleavage with EcoRI, in all cases, decreased the yield to less than 10%. This further demonstrates that the material can be used directly for restriction analysis and further suggests that the material can be used for recombinant DNA application.

To test the degree of contaminations between the different preparations overnight cultures of E.coli HB101 containing pUC8 or pBR 322 (Maniatis et al., see above) were purified as described above. The automated purification was performed with pUC8 samples as number 1, 3, 5 and 7 and pBR322 as 2, 4, 6 and 8. The uncleaved plasmid fractions were transformed into competent E.coli HB101 and, in addition to selection on ampicillin plates, also selected on plates containing tetracyclin (8 mg/l). Plasmid pUC8 can only confer ampicillin resistance, while pBR322 confers both ampicillin and tetracyclin resistance to its host bacteria. The results demonstrate that the contamination of tetracyclin resistant clones for the pUC8 purified material is in all cases less than 0.1%.

We claim:

1. Method for automatic separation and recovery of extra-chromosomal DNA from a bacterial cell suspension, comprising
 introducing the bacterial cell suspension into a chamber,
 introducing a lysing solution into the chamber and mixing it with the contents thereof to lyse the cells therein,
 introducing a precipitating solution into the chamber and mixing it with the contents thereof to precipitate chromosomal DNA, proteins and cell debris therein,
 filtering the liquid contents of the chamber through a filter for removing precipitated protein, chromosomal DNA and cellular debris and feeding the filtered liquid to a collecting device,
 recovering extra-chromosomal DNA from the contents of the collecting device in the substantial absence of precipitated protein, chromosomal DNA and cellular debris,
 introducing a dissolving solution into the chamber and mixing it with the contents thereof to dissolve the precipitate remaining therein, and feeding the dissolved precipitate from the chamber to waste.

2. Method according to claim 1 wherein the temperature of the chamber is raised an effective amount to enhance the lysis of the cells, and the temperature is then lowered an effective amount to enhance precipitation during the precipitation of the chromosomal DNA, proteins and cell debris.

3. Method according to claim 1, comprising using pressure to indice the flow of liquids.

4. An apparatus for separating and recovering plasmid DNA from bacterial cells which contain plasmid DNA and chromosomal DNA; said apparatus comprising:

a) a mixing chamber having a plurality of inlet and outlet ports for the passage of fluid therethrough and means for controlling the temperature of said chamber;

b) an agitator in said mixing chamber;

c) a first multi-port set of valves having a plurality of inlet and outlet ports;

d) a lysing solution container and a conduit which connects said lysing solution container to an inlet port of said first multi-port set of valves for the passage of lysing solution therethrough;

e) a precipitating solution container and a conduit which connects said precipitating solution container to an inlet port of said first multi-port set of valves for the passage of precipitating solution therethrough;

f) a vacuum pump which is connected to an outlet port of said first multi-port set of valves;

g) a bacterial cell suspension container and a conduit which connects said bacterial cell suspension container to an inlet port of said first multi-port set of valves for the passage of bacterial cell suspension therethrough;

h) a conduit which connects an outlet port of said first multi-port set of valves to an inlet port of said mixing chamber for the passage of lysing solution, precipitating solution and bacterial cell suspension into said mixing chamber;

i) a waste conduit connected to an outlet port of said first multi-port set of valves for the elimination of waste therefrom;

j) a second multi-port set of valves having a plurality of inlet and outlet ports for the passage of fluid therethrough;

k) a conduit which connects an outlet port of said mixing chamber to an inlet port of said second multi-port set of valves for the passage of fluid therethrough and means for filtering precipitated chromosomal DNA, protein and cellular debris from said fluid which passes therethrough for the production of a filtered fluid which contains dissolved plasmid DNA in the substantial absence of chromosomal DNA, protein and cellular debris;

l) a sample collector for collecting the filtered fluid containing the dissolved plasmid DNA; said sample collector having an inlet and an outlet, set inlet of the collector being connected to an outlet port of said second multi-port set of valves for receiving said filtered fluid and said outlet of the colletor being connected to an inlet port of said second multi-port set of valves for returning said filtered fluid to said second multi-port set of valves;

m) means for recovering the plasmid DNA, said means for recovering the plasmid DNA being connected by a conduit to an outlet port of said second multi-port set of valves for the passage of filtered fluid from the sample collector to the plasmid DNA recovery means via the second multi-port set of valves;

n) a dissolving and cleaning solution container and a conduit which connects said dissolving and cleaning solution container to an inlet port of said second multi-port set of valves for the passage of dissolving and cleaning solution therethrough;

o) a conduit which connects the second multi-port set of valves with the mixing chamber for passing the dissolving and cleaning solution from the second multi-port set of valves through said filter means and into the mixing chamber; and p) a conduit which connects an outlet port of said mixing chamber to an inlet port of said first multi-port set of valves for drawing bacterial cell suspension into said mixing chamber by action of said vacuum pump and for the elimination of the dissolving and cleaning solution through the waste conduit via the first multi-port set of valves.

5. The apparatus of claim 4 wherein the means for recovering the plasmid DNA is a chromatographic gel filtration column.

6. The apparatus of claim 4 which further includes means for air pressurizing the lysing solution container, the first multi-port set of valves, the precipitation solution container and the dissolving and cleaning solution container.

7. The apparatus of claim 6 wherein the means for air pressurizing is a source of pressurized air connected by conduits to the lysing solution container, the first multi-port set of valves, the precipitation solution container and the dissolving and cleaning solution container.

8. The apparatus of claim 4 wherein the collector is in the form of a looped tube.

9. The apparatus of claim 5 which further includes an eluent container with a pump attached thereto which is connected to the second multi-port set of valves through a conduit for the passage of eluent into the filtration column via the second multi-port set of valves.

10. The device of claim 4 wherein the filtering means is a filter located in the bottom of the mixing chamber.

* * * * *